(12) United States Patent
Shcherbinin et al.

(10) Patent No.: US 11,710,625 B2
(45) Date of Patent: Jul. 25, 2023

(54) UNBIASED ION IDENTIFICATION BY MULTIPLE IONS

(71) Applicant: Karsa Oy, Helsinki (FI)

(72) Inventors: Aleksei Shcherbinin, Helsinki (FI); Jyri Mikkilä, Helsinki (FI); Matti Rissanen, Helsinki (FI); Oskari Kausiala, Tampere (FI)

(73) Assignee: KARSA OY, Helsinki (FI)

( * ) Notice: Subject to any disclaimer, the term of this patent is extended or adjusted under 35 U.S.C. 154(b) by 0 days.

(21) Appl. No.: 17/527,721

(22) Filed: Nov. 16, 2021

(65) Prior Publication Data
US 2022/0157585 A1    May 19, 2022

(30) Foreign Application Priority Data

Nov. 17, 2020   (FI) ..................................... 20206161

(51) Int. Cl.
| | | |
|---|---|---|
| *H01J 49/00* | (2006.01) | |
| *G01N 33/497* | (2006.01) | |
| *H01J 49/02* | (2006.01) | |
| *H01J 49/04* | (2006.01) | |
| *H01J 49/14* | (2006.01) | |

(52) U.S. Cl.
CPC ........ *H01J 49/0031* (2013.01); *G01N 33/497* (2013.01); *H01J 49/0036* (2013.01); *H01J 49/025* (2013.01); *H01J 49/0422* (2013.01); *H01J 49/145* (2013.01)

(58) Field of Classification Search
CPC .. H01J 49/0031; H01J 49/0036; H01J 49/025; H01J 49/0422; H01J 49/145; H01J 49/107; H01J 49/10; G01N 33/497; G01N 27/62

USPC ......................................... 250/281, 282, 288
See application file for complete search history.

(56) References Cited

U.S. PATENT DOCUMENTS

| | | | |
|---|---|---|---|
| 2004/0089802 A1* | 5/2004 | Kato ................... | H01J 49/0045 250/288 |
| 2004/0195500 A1* | 10/2004 | Sachs ..................... | G16B 40/10 250/282 |
| 2007/0057178 A1 | 3/2007 | Chernushevich et al. | |

(Continued)

FOREIGN PATENT DOCUMENTS

| | | |
|---|---|---|
| EP | 2 927 930 | 10/2015 |
| EP | 3 629 364 | 4/2020 |
| GB | 2 362 259 | 11/2001 |

(Continued)

OTHER PUBLICATIONS

Finnish Office Action for 20206161 dated Jun. 10, 2021, 7 pages.

(Continued)

*Primary Examiner* — Michael Maskell
(74) *Attorney, Agent, or Firm* — Nixon & Vanderhye (57) ABSTRACT

Disclosed are embodiments directed to a multi-ion identification device, a system and method using the same to utilize chemical ionization in multiple adduct formation from the substances in the sampled gas of a gas sample being addressed to be analyzed in a mass analyzer. The multi-ion identification device includes a buffering region to have the sample flow turbulence decayed before the sample flow entrance to the ionization region)) utilizing chemical ionization by reagents from an ensemble of reagent ion towers.

20 Claims, 4 Drawing Sheets

(56) References Cited

U.S. PATENT DOCUMENTS

2008/0116369 A1    5/2008  McCauley et al.
2016/0126079 A1*   5/2016  Sipilä .................... H01J 49/145
                                                          250/288

FOREIGN PATENT DOCUMENTS

| WO | 99/65058 | 12/1999 | | |
| WO | 2006/107831 | 10/2006 | | |
| WO | 2018/050962 | 3/2018 | | |
| WO | WO-2018050962 A1 * | 3/2018 | ............... | B05B 1/00 |

OTHER PUBLICATIONS

Finnish Search Report for 20206161 dated Jun. 10, 2021, 2 pages.
European Search Report issued in European Patent Application No. 21 20 8548 dated Apr. 7, 2022.

* cited by examiner

UNBIASED ION IDENTIFICATION BY MULTIPLE IONS

This application cairns priority to Finnish Application No. 20206161 filed Nov. 17, 2020, the entire contents of which are hereby incorporated by reference.

BACKGROUND OF THE INVENTION

Field of the Invention

Generally, the present invention relates to ion identification from a medium being sampled to the ion identification device. In particular, the present invention pertains to a multi-ion identification device to determine a composition of gaseous species in the sampled medium to be analyzed to identify the ions and so to determine the composition of the sample. The present invention relates also to such a program product that is used in the control of said ion identification by the multi-ion identification device. The present invention relates also to a system to produce a database being formed from the measurement results being made by the system.

DESCRIPTION OF THE RELATED ART

Determination of various gaseous compositions comprising organic constituents in the gases has been made in the history in 150 years as such. One example of an early composition study relates to Breath analysis dates to 1874 when Francis E. Anstie made the first observations that alcohol could be detected in excreted breath air. This was of little functional use at the time, but the first breathalyzer was invented in 1927 and the first practical roadside test was commercialized in 1931 with the first electronic version being developed in 1967.

In current clinical settings some diagnoses can be aided through breath screening devices (e.g. asthma), however, the promise of accurate diagnosis of many conditions, just by blowing into a tube, has been much vaunted, but never achieved, leading to certain skepticism within clinical community to have such a device to assist to provide sufficient compositional information to be used in the analysis by the professional persons.

Instant diagnosis and screening of medical conditions has always been a dream of science fiction, from the tricorder in 'Star Trek' to the diagnostic bed, a staple of many sci-fi stories. These tools, even today, still seem to be decades away, but recently breath analysis has been showing a promise to have a diagnose being based on data obtained by certain limited conditions in a non-invasive way. There is a question what prevents devices to breath analysis from becoming these truly universal diagnostic tools for the professional persons? For one, chemical complexity of human breath as exhaled is beyond the limitation of current analysis techniques, such as Gas Chromatography (GC) and Proton Transfer Reaction Mass Spectrometry (PTR-MS). Although these devices and systems have excellent analytical capabilities and have been used for decades they seem to struggle when it comes to detecting more functionalized and less volatile compounds in gas sample, a class of molecules that may in fact become the cornerstones of breath analysis data to be used. However, as these tools can only detect a certain range of compounds, and only within a limited scope, this is one of the limiting factors that has slowed the development of breath analysis as a usable and universal tool for professional persons to make diagnostics. More information on the limitations of these systems come mainly from (i) sampling of semi-to-low-volatile material and (ii) limit of detection due to poor ionization efficiency, for example.

Artificial intelligence was also once a science fiction trope that showed how the halcyon days of the future would be cushioned by AI support, anticipating the needs of users and providing information and support on a just in time basis. Whereas this AI was unthinkable 20 years ago, nowadays AI and machine learning, that can teach itself and become more useful with little human input, is becoming standard. With the many examples of AI that can be seen in modern times, such as better traffic management, to entertainment services, to enhanced fraud detection, these all need one common element to make them work. Data. Lots of data.

A decade ago, breath analysis was a promising emerging technology that aspired to become the new screening tool in the medical arsenal to detect diseases that are hard to diagnose or otherwise screen for. Some progress has been made over the past years, but the promise remains unfulfilled and medical practitioners and clinicians have become sceptical[1]. A functional breath test is a convenient and minimally invasive method for detection of certain compounds in exhaled breath which could be used for material for producing data for diagnosis of certain conditions and health risks. Currently, only a few breath analysis tools have made it to mainstream clinical practice.

Recent systematic review and meta-analyses of Volatile Organic Compounds (VOC) based breath tests for cancer diagnosis revealed lack of methodological standardization while mentioning that tests have potential for non-invasive cancer diagnosis[2]. A framework for conducting and reporting future studies investigating the role of VOCs in cancer diagnosis was proposed by the authors of the review. However, research have shown that previous attempts may have had methodological problems that could lead to overestimation of VOC-based breath tests performance[3]. This criticism focused mainly on methodological problems. The analysis of VOCs that differ between two groups of study participants (e.g. diseased and healthy) is often the primary aim of such studies, while the origin and the pathophysiological significance of the identified marker compounds have been frequently neglected[4]. Breath-atlas proposes radically different approach where the first question asked is: what chemical compounds constitute normal human breath?

Human breath contains hundreds of different volatile compounds and the distribution varies from one person to another. Some compounds in exhaled breath are the results of environmental exposure, others are generated by the normal metabolism of the body, and still others are the products of bacterial or viral infections or other medical conditions.

Exhaled breath is a complex gas mixture with hundreds (potentially many thousands) of analytes and the concentrations of the biomarkers are often very low (in the part-per-billion (PPB) or part-per-trillion (PPT) range, from those that are known). To target virtually every gas-phase chemical compound, a collection of ionization reagents is needed. With increasing functionalization of a molecule, simple molecular parameters become less well defined. One simple example is offered by amino acids, which have characteristically both acidic and basic functionalities, with the acid-base behavior changing depending on the structure of the rest of the molecule.

There is widespread need for an advanced online chemical analysis of gaseous samples: from detecting explosives, to screening food samples for presence of pesticides, to environmental monitoring, to diagnosing diseases from breath. There is one major shortcoming that hinders chemical technology to achieve that and become more than a tool for research. Real world problems usually include detecting multiple compounds from very different chemical classes, for instance from very polar and acidic to less functional compounds. Each technique like PTR, GC or APCI has it's limitations in terms of what kind of molecules they are best to distinguish and identify and changing between the set-ups is hard and laborious, and may take hours or days. Present invention proposes a way to overcome this problem and provide set of tools for unbiased and standardized analysis of gaseous samples for chemical composition.

SUMMARY OF THE INVENTION

The objective is to at least alleviate the problems described hereinabove not satisfactorily solved by the known arrangements, and to provide a feasible multi-ion identification device to be used in gaseous composition sample analysis, to reveal also such more functionalized and less volatile compounds to be identified and analyzed for the data about the composition and the abundances of those molecules in it, as well as provide information on more volatile less functionalized compounds simultaneously without the need to change the setup and interrupt sampling.

Mass spectrometers are analytical instruments that can be used to analyze the chemical composition of air with high precision. The problem is they only measure ions, which means that the molecules need to be charged (ionized) first. Several ionization techniques have been developed, each one with their own characteristics and applications.

Chemical ionization (CI) is a method in which a reagent chemical is used to produce reagent ions, that are mixed with the air sample. It is a soft ionization method using such mechanism, meaning that the molecules of interest will stay intact and cluster with the reagent ion. This greatly helps with detection, because the elemental composition of the target molecule generally does not change. Another important aspect of chemical ionization is selectivity. Certain reagent ions tend to cluster only with molecules having distinct properties. Selectivity is both a good and a bad thing. It allows for great sensitivity when the target molecule has the tendency to cluster with the selected reagent ion, because majority of the molecules in the air are not ionized and thus noise level is low.

However, the obvious drawback is that a certain reagent only works for limited number of molecules, and as such, it is not a suitable method for detecting a broad range of chemicals with varying properties.

Another complication of using conventional CI and SESI (Secondary Electrospray Ionization) is neutral reagent vapors/droplets mixing with sample flow, which alters the sample chemistry and complicates using more than one ionization scheme.

The aforesaid objective is achieved by the embodiments of a multi-ion identification device, to be used in a system and method of comprehensive data analysis in accordance with the present invention. It is in the interest of the applicant to build a ground-breaking tool for online gas phase analysis that will not only improve detection of the known compounds in air, such as found in exhaled breath, but open a possibility to study molecules that has been only anticipated in theory and never before measured in practice so far in a systemic and standardized method and provide researchers using said devices with a knowledgebase on gas phase chemistry that will evolve with time.

It is the machine learning algorithms (such as deep learning) to be used in analysis of this data and the comparison of data in huge sets that allows the software to recognize patterns of the constituents and suggest to react accordingly, in order to deliver analysis of complex patterns within sample chemistry and create classification predictions, such as deriving underlying conditions that lead to particular chemical composition.

The disruptive approach can be made by employing an embodied online system of the present disclosure to provide APCI-OT-MS (Multi Ion Atmospheric Pressure Chemical Ionization Orbitrap Mass Spectrometer (i.e. MION APCI-OT-MS) or any other suitable ion detection device as a detector, such as IMS which simultaneously utilizes multiple selective ion chemistries both in negative and positive modes of detection, which enables the system to detect a wide range of very different chemical classes with unprecedented sensitivity and selectivity. Thus, providing a possibility of unbiased and comprehensive chemical analysis of gaseous samples.

According to an embodiment, a Multi Ion Atmospheric Pressure Chemical Ionization Orbitrap Mass Spectrometer (MION APCI-OT-MS) is capable of detecting virtually every gas phase molecule potentially present in human breath at unprecedented sensitivity. Using an embodied system comprising a MION APCI-OT-MS, will develop a gas sampling methodology suitable for large scale quantitative analysis of the composition breath as an example (accounting for exhaled volume, relative humidity and other underlying conditions affecting the spectral signal). But also suitable for example for ambient environmental measurements.

At the same time, other tools can be used for collecting comprehensive auxiliary metadata to a database being developed, allowing for multifactor analysis of the acquired breath spectra and their composition. Next, further measurement data is collected. This innovative and unique approach according to the embodiments of the present disclosure gives the possibility for detection of a wide range of chemical compounds previously not detected with conventional tools. This unbiased sampling of the compositional information in the sample, such as breath for example, reveals the components for optimization the resolution and predictivity in a similar way as broad expression genomic and expression-based chemistry for example cancer analysis was needed to enable new, would provide means for personalized treatments being order as based on the analysis made by the medical professionals aided by the data being created by embodiments of the present disclosure.

Specific algorithms can be used in the embodied system with a dedicated configuration to apply 'big data' techniques and Machine Learning Algorithms (MLA) to analyze the data obtained from the samples being sampled by the embodiments of the present disclosure, i.e. that has been collected through the breath sampling and the auxiliary complementary data and attempt to correlate specific chemicals found in breath with different sociomedical attributes related to the composition. Embodiments can make such work done applying multivariate statistical methods for identification of patterns of breath markers in gas compositions of both healthy individuals and for the study of the gas compositions of breath-based disease networks (e.g. asthma, cancer, and other lung pathologies) to provide the data for professionals to make diagnosis as based on the data.

The aforesaid objective(s) are achieved according to the present invention as claimed in claim 1.

A multi-ion identification device according to an embodiment of the disclosure of the present invention is characterized in that the device comprises a first plurality of reagent ion towers in a first plane perpendicular to sample flow entrance direction to ionization region of the multi-ion identification device, a second plurality of reagent ion towers in a second plane perpendicular to sample flow entrance direction to ionization region of the multi-ion identification device, wherein said first plane and second plane being parallel by the reagent tower positions to provide a reaction time for the ions emitted from the respective reagent ion towers to chemically ionize analyte molecules in the sample, the so formed adducts in chemical ionization being transported from the ionization region to a mass spectrometer port to exit from the ionization region of the device for mass analysis of the adducts.

According to an embodiment of the present disclosure, at least one of the sheath flows is made to occur in laminar flow regime. According to an embodiment variant, the sheath flows are controlled to the laminar flow profile shape by equalizing their velocities. According to an embodiment, in an embodiment of the present disclosure, there is a flow shaper (i.e. a mesh or a number of consecutive meshes in the flow direction) for making each sheath flow laminar, to further fine tune the shape of the sheath flows to make sure that each sheath flow has laminar character in the laminar flow regime.

According to an embodiment, a humid gas sample can be dried by a dryer as means for drying the sample flow by diffusional drying. According to an embodiment of the present disclosure, in an embodied multi-ion identification device each ionization reagent of the respective reagent ion tower in same plane (IR(A)) is configure to operate according to same ion production mechanism to provide respective reagent ions from a dedicated reagent ion tower.

According to an embodiment of the present disclosure, in an embodied multi-ion identification device the ionization mechanism of a reagent ion tower is at least one of the following: X-ray, soft-X-ray, corona discharge, and electrospray based mechanism(s).

According to an embodiment of the present disclosure, in an embodied multi-ion identification device the polarity of a reagent ion tower produced ions are adjustable to positive or negative ions. According to an embodiment variant, a reagent ion tower can be controlled to neutral polarity, i.e. non-positive or non-negative polarity.

The polarity can be changed by switching the charging mechanism for example, but also in addition by filtering the non-wanted ions by electric field out of reach of the exit of the reagent ion tower in question.

According to an embodiment of the present disclosure, in an embodied multi-ion identification device, at least one of the reagent ion towers comprises a filter to filtrate multiply charged reagent agents or unwanted polarity carrying reagent ions away from entry to the ionization region. According to an embodiment, the filter is based on electrostatic fields. According to an optional embodiment, the filter is based on ion trap with alternating electric field. According to an embodiment, the ion trap filter has in addition to alternating electric field an electrostatic field arranged to trap reagent ions to the ion trap.

According to an embodiment of the present disclosure, in an embodied multi-ion identification device the ionization region comprises a round cylindrical symmetry with a centerline (C) as a symmetry center. According to an embodiment, the multi-ion identification device comprises a buffering region. According to an embodiment, the buffering region has same symmetry axis as the ionization region. According to an embodiment, the buffering region has a length sized to flow velocity for a sample flow turbulence decay to laminar flow regime for the sample flow at the entry to ionization region. According to an embodiment, each sheath flow velocity at the buffering region entrance to enter ionization region has been matched to settle to laminar flow conditions. According to an embodiment each sheath air flows are adjusted to the flow velocity of the sample flow velocity. According to an embodiment, the adjustment is made by the control unit, according to an embodiment by the user, but according an optional embodiment by the software arranged to adjust sheath flow valve as a sheath flow actuator.

According to an embodiment of the present disclosure, in an embodied multi-ion identification device the reagent ion towers are aligned in to a plane, and have an off-set ($\alpha$) to deflect from the direction of the ionization region centerline along the respective emitting lines pointing radial directions.

An multi-ion identification system according to an embodiment of the present disclosure of the invention, an embodied multi-ion identification system comprises:
- at least one multi-ion identification device according to an embodiment of the present disclosure of the invention,
- control unit to control the multi-ion identification system and its actuators for the operation in mass analysis of adducts formed from the constituents of the sample,
- a mass spectrometer to make said mass analysis,
- a database to store mass analysis results.

Embodied system is also referred as MION-system.

According to an embodiment of the present disclosure of the invention, an embodied multi-ion identification system comprises a software packet configured to control operation of the multi-ion identification system. According to an embodiment, the software packet comprises the software of the control unit, to control the actuators of the system. According to an embodiment, the control unit is arranged to maintain the flows of the multi-ion identification device, voltages and/or the environmental quantities. According to an embodiment, the control unit is arranged to operate the spectrometer as a system element. According to an embodiment, the software packet is configured to constitute a database for the measurement results, obtained by the mass spectrometer in control of the control unit in measurements. According to an embodiment, the software packet is configured to provide an machine learning algorithm and number of statistical tools, which can have a self-learning packet for data analysis to make cluster analysis and/or to find marker substances from the composition data of the samples and/or mass spectrometer signals.

According to an embodiment of the present disclosure of the invention, an embodied multi multi-ion identification system comprises such a software packet (SW) that is configured to make group analysis from the clusters to find and deduce marker substances and/or newly found molecules, such as HOMs for example, from the results. These HOMs (Highly Oxidized Multifunctional organic molecules) can comprise hundreds of different types of molecules that were seldom detected, if never before at all, as components of secondary aerosol. According to an embodiment of the present disclosure of the invention, an embodied software packet for the embodied multi-ion identification system comprises at least one of the following: a machine learning algorithm, a neuron network solver for optimization of cluster analysis, an artificial intelligence algorithm, such as penalized linear LARS, an elastic net regressions algorithm, random forests and recursive feature elimination algorithm.

According to an embodiment, the system comprises an ion detector to detect ions, said ion detector as embodied for example as Ion Mobility Spectrometer, (IMS), or as mass spectrometer, such as a Multi Ion Atmospheric Pressure Chemical Ionization Orbitrap Mass Spectrometer (MION APCI-OT-MS) being configured to simultaneously utilize multiple selective ion chemistries both in negative and positive modes of detection.

According to an embodiment of the present disclosure of the invention, an embodied multi-ion identification system comprises such a mass spectrometer as a system element that is a Multi Ion Atmospheric Pressure Chemical Ionization Orbitrap Mass Spectrometer (MION APCI-OT-MS) being configured to simultaneously utilize multiple selective ion chemistries both in negative and positive modes of detection.

According to an embodiment of the present disclosure of the invention, an embodied multi-ion identification system comprises in the system configuration to detect extremely low vapor pressure, highly oxidized multifunctional organic molecules (HOM) from the sample.

A method of identifying substances from a gas sample by using a MION-system according to an embodiment comprises:
 sampling a gas sample into a sample flow of the multi-ion identification device,
 allowing turbulence to decay to laminar flow conditions of the sample flow in a buffering region of the multi-ion identification device,
 protecting the gas sample by at least one or two sheath flows at least in the buffering region,
 charging the gas sample constituents by reagent ion molecules formed for use in chemical ionization of said gas sample constituents to form adducts,
 allowing the adduct to form from the gas sample constituents and reagent ion molecules,
 leading the adducts to mass spectrometer for mass analysis,
 identifying the adducts and the gas sample constituents,
 storing to a database the identified gas sample constituents.

According to an embodiment, the method can comprise finding similarities from the database with similar samples, as based on identified marker substances from the previous sample mass spectra in the database. In addition, in the embodiment variant of the method, the sample associated additional data is compared to similar associated additional data of the previous samples to find correlations from the additional data and the markers between the instant and previous gas samples. According to an embodiment, the comparison is made by the software packet as a system element. According to an embodiment variant the comparison comprises at least one of the following being used in it: an artificial intelligence algorithm to find patterns between the addition data and the marker substances, self-learning algorithm to assist the artificial intelligence algorithm, and neural network for optimization of the finding the marker substances.

According to an embodiment, database is in cloud, the system elements of the embodied system can constitute a network of systems contributing to the database to make it more rigorous. Individual terminals as system elements can access to the database via network. Edge computing (where the system is) will identify peaks in the chemical spectra, neural network can be embodied to be in the cloud in the main database, in suitable part, and according to an embodiment the cloud integrates the database with other data and provide analysis, for example meta data classification prediction, for example underlying condition corresponding to chemical composition of breath.

The expression "a number of" refers herein to any positive integer starting from one (1), e.g. to one, two, or three.

The expression "a plurality of" refers herein to any positive integer starting from two (2), e.g. to two, three, or four.

The expression to comprise has been used as an open expression.

Different embodiments of the present invention are disclosed in the dependent claims.

BRIEF DESCRIPTION OF THE DRAWINGS

Next embodiments of the present disclosure according to the invention are described in more detail with reference to the appended drawings in which.

DESCRIPTION OF THE PREFERRED EMBODIMENTS

Same reference numerals in different figures can be used to refer to similar objects, which do not necessarily be exactly identical, as a skilled person in the art understands from the embodiments of the invention.

Figure 1:
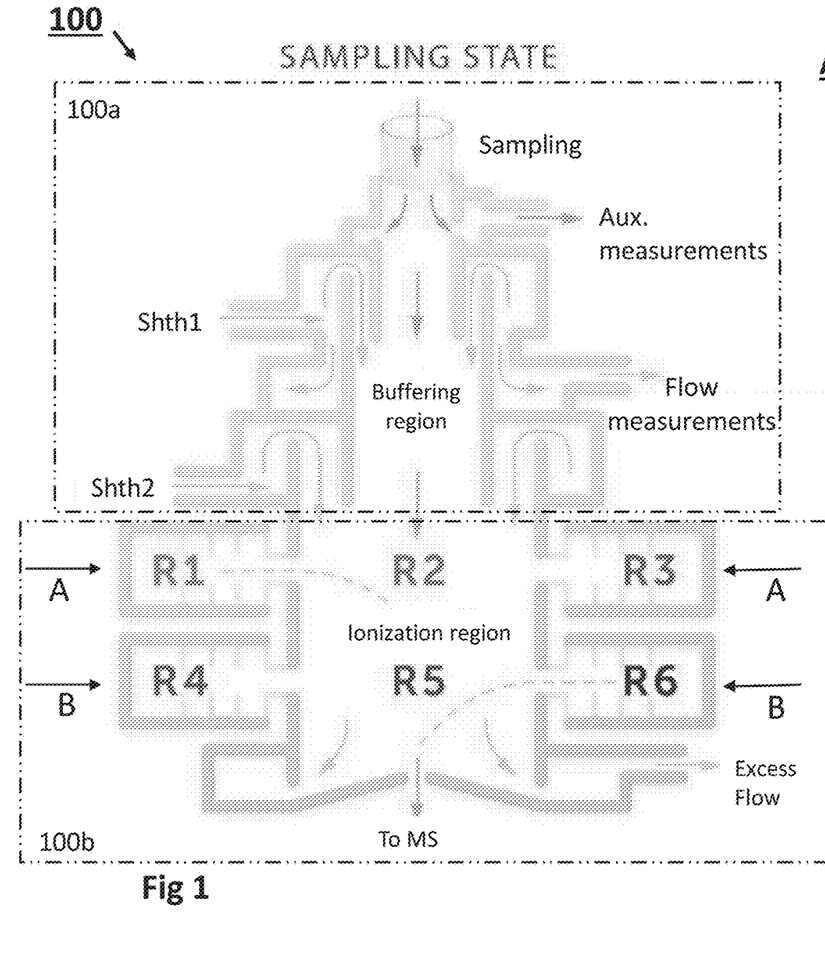
FIG. 1 illustrates an exemplary embodiment of an multi-ion identification device in accordance with the present disclosure of the invention, in a sampling state to be embodied with one or more embodiments of the invention.
Figure 4:
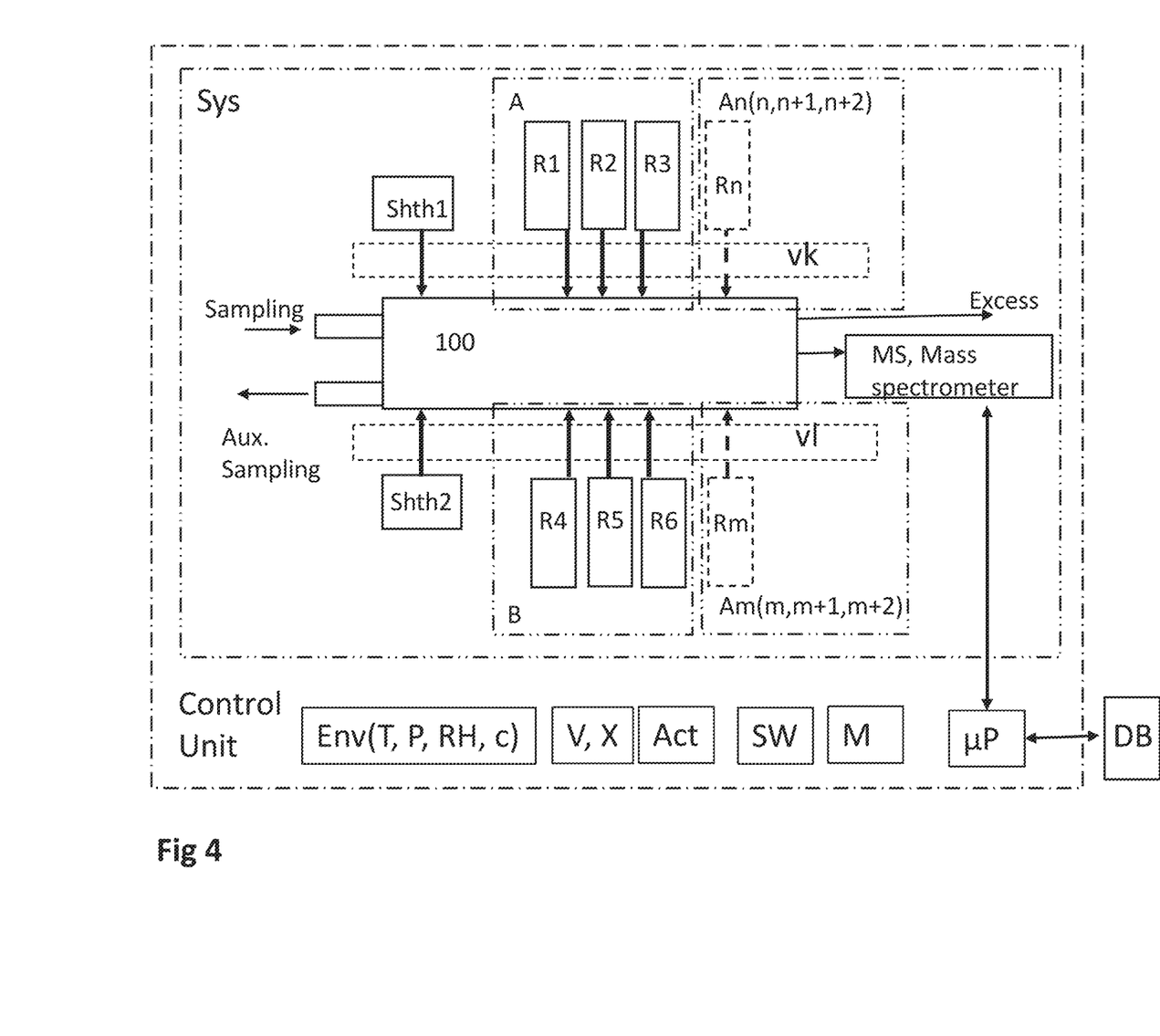
FIG. 4 illustrates a MION system as an exemplary embodiment to use an multi-ion identification device in accordance with the present disclosure of the invention, to be embodied with one or more embodiments of the invention.

FIG. 1 illustrates multi-ion identification device 100 of a MION-system (Sys, FIG. 4), to be used with co-operation of a mass spectrometer MS (FIG. 4).

According to an embodiment, in the multi-ion identification device 100, there is a buffering region 100a, in which the sheath flows enter to the multi-ion identification device, as well as the sample to the device. According to an embodiment, the buffering region can comprise a port to auxiliary measurements to further processing of the sample elsewhere and/or a redundant and/or a diverse analysis elsewhere, i.e. in a second device which can be similar, but is not necessarily the same.

The total flow can be measured at the port Flow measurement, as based on the direct measurement of the flow and/or the set flows in the other parts of the device according to the set up made by the control unit to control flow actuators in the system. The arrows in FIG. 1 illustrate flows, and the curved dashed lines paths of dedicated reagent ions from the corresponding reagent ion towers (R1, R6).

Reagent ion towers (R1, R2, R3, R4, R5, R6, Rn, Rm) can be embodied with acceleration and filtration of ions according to their charge. Reagent ion towers can charge reagent substances, being fed according to their dedicated feeds from the corresponding reagent substance sources, the feed and/or species being controlled by the control unit. The reagent ion towers, (also as ion towers) can utilize in the reagent charging soft x-rays, corona discharge and/or electrospray-mechanisms, to provide the reagents with wanted polarity to be used in the ionization region to chemically ionize sample molecules by the reagent molecules adducting to the sample molecules.

The sheath flows sheath1 and Sheath2 are arranged to follow the cylindrical geometry of the buffering region of the device, so that both sheath flows are introduced into the buffering region to form an annular sheath surrounding the sample flow, according to an embodiment the geometry and the flows being set so that the sheath flows and the sample flow has equal velocity, so to prevent unwanted vertical vortex mixing and/or turbulence formation. According to an embodiment, the flows are set to correspond laminar flow conditions by the control unit controlling the flow valves as flow actuators as system elements, under the surveillance of the software packet routines dedicated to flow maintenance.

Figure 2:
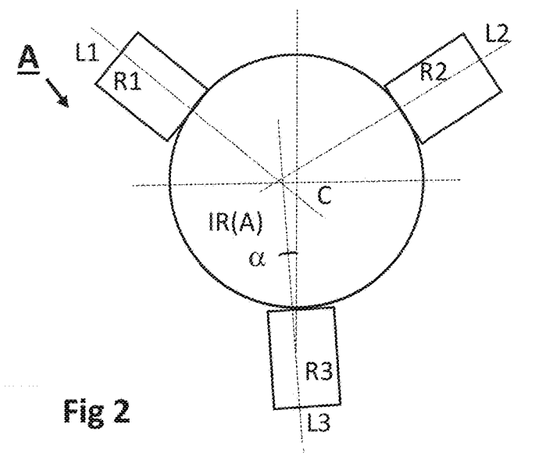
FIGS. 2 and 3 illustrate as examples of ion injection towers as reagent ion towers in layers of an embodied multi-ion identification device in accordance with the present disclosure of the invention, to be embodied with one or more embodiments.
Figure 3:
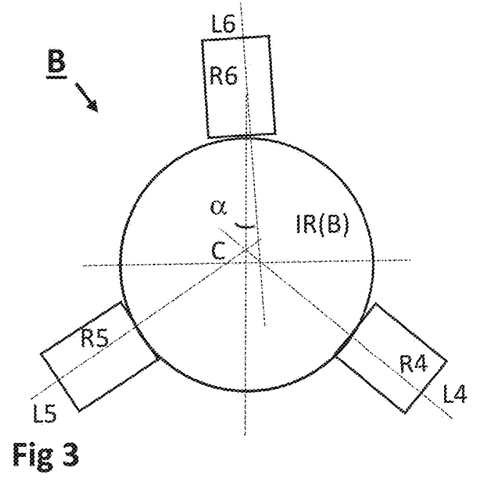

FIGS. 2 and 3 illustrate each a section of the ionization regions (IR(A) and IR(B)) at the levels A and B. In FIG. 2, the capital C represents the geometric center line of the ionization region 100b at the level IR(A). The same geometric center axis line equals the geometric symmetry axis line of the buffering region 100a.

At the level IR(A), the lines L1, L2 and L3 represent the planar lining of the corresponding respective reagent ion towers R1, R2 and R3, so that R1 is lined along the L1 to inject ions to the direction indicated by the line L1. According to an embodiment of the invention of the present disclosure, the lines L1, L2 and L3 are misaligned (i.e. having an off-set) in a radial manner from the geometric center direction, by a sharp angle $\alpha$.

According to an embodiment the angle is below 30°, according to an embodiment variant below 20°, according to a further variant below 10°, according to even further variant below 5°, but according to an embodiment variant between 0.7° to 35°

Similar geometry as at the level IR(A), at the level IR(B), the lines L4, L5 and L6 represent the planar lining of the corresponding respective reagent ion towers R4, R5 and R6, so that R4 is lined along the line L4 to inject ions to the direction indicated by the line L4. According to an embodiment of the invention of the present disclosure, the lines L4, L5 and L6 are radially misaligned (i.e. having an off-set) from the geometric center (capital C) direction, by a sharp angle $\alpha$.

According to an embodiment the angle is below 30°, according to an embodiment variant below 20°, according to a further variant below 10°, according to even further variant below 5°, but according to an embodiment variant between 0.7° to 35°.

According to an embodiment, the misalignments selected to deflect between levels A and B, especially in such embodiments, in which the level R3 and R6 would be oppositely mounted to their respective own levels. According to an embodiment, such a misalignment is made on purpose to certain degree, to prevent the oppositely placed reagent ion towers (i.e. as exemplified to different levels the R3 and R6) to adversely affect each other's operation in the chemical ionization. According to an embodiment the off-set is made to same direction of rotation, so prevail a certain kind of equal sectors for the ionization probability with similar reaction times at the level, with equal efficiency to get the sample analyte to be charged by the reagent ions at the ionization region's sub-region.

According to an optional embodiment variant, the lines L1, L2 and L3 could be provided for such a mounting of R1, R2 and R3, so that lines L1, L2 and L3 would define a first conical mantel. However, such an embodiment would produce different ionization relaxation times to settle more easily to different parts of the ionization region than when planar. Such embodiment could be useful if such effect would be desired.

According to an optional embodiment variant, the lines L4, L5 and L6 could be provided for such a mounting of R4, R5 and R6, so that lines L4, L5 and L6 would define a second conical mantel. However, such an embodiment would produce different ionization relaxation times to settle more easily to different parts of the ionization region than when planar. Such embodiment could be useful if such effect would be desired. However, the first and second conical mantels as defining the reagent ion tower direction need not necessarily to be co-aligned.

In FIGS. 2 and 3 three angularly equally distributed injection towers as reagent ion towers are embodied in each level IR(A) and IR(B), as an example of the number and angular position of them. A skilled person realizes from these example embodiments, that the number of injection towers as reagent ion towers is not limited necessarily only to three per level, but can be varied to greater number, such as four, five or six according to the respective embodiments. The off-set can be embodied according to that what has been discussed with the R1, R2 and R3 concerning their off-sets. As skilled person in the art realizes also that the member of the levels (A, B) is not necessarily limited only the shown two, but can be according to the respective embodiment variants three, four or five, however, taking into account diffusion characteristics of the sheath gas material as well as the expected sample composition, to provide accordingly sufficient crosstalk suppression by the embodied number of reagent ion towers and purge time characteristics for each.

The indicated flows (Shth1, Shth2, Excess, as well as Flow measurement flow to a flow measuring device and the flow to the Aux. measurement) can be controlled by a Control unit (FIG. 4), under command of a software packet (SW, FIG. 4) for the MION system (Sys, FIG. 4), the software piece of the software packet being run by a dedicated microprocessor ($\mu$P, FIG. 4) of the system to control the system operations. There are embodied Shth1 as the sheath flow 1 and Shth2 as the sheath flow 2 to be used for sheathing the sample constituents travelling in the buffering region to enter the ionization region 100b, the sheath flows being controlled by the control unit (FIG. 4) by using suitable ensemble of flow-dedicated actuators, so that for example an actuator to control Sheath flow 1 (Shth1) is dedicated to control the flow independently on the other flows as such, but however so that the set values to each flow under the control in whole represent a meaningful flow value being set by each flow-dedicated actuator, so that the sample flow is led through the multi-ion identification device 100 towards the mass spectrometer MS leading port. According to an embodiment, the sheath flows Shth1 and Shth 2 are used to protect the sample carrying flow through buffering region to ionization region.

According to an embodiment, the sheath flows are matched to laminar flow geometry to annularly surround the sample flow, so that the Shth1 surrounds the sample flow and the Shth2 surrounds the Shth1 and consequently also the sample flow at a distance. According to an embodiment the flow rate of the sample flow, sheath flow 1 and sheath flow 2 are set so, that they progress adjacently through the ionization region. These flows are set by the control unit (FIG. 4).

These actuators to be controlled as such as well as other actuators in the system are illustrated in FIG. 4 by the actuator Act, referring a group of actuators for various purposes to maintain the operation of the system and its system elements.

Such actuators can be also used to control the operating environment of the device, to be used according to the ambient conditions, but also optionally to be operated in set conditions inside the device 100, by controlling the temperature (T), Pressure (P), relative humidity (RH) and/or composition (c) of the sheath gas of at least one of the sheath flow 1 and sheath flow 2. The controlling can be implemented by an ensemble of valves vk and/or another ensemble of valves vl, being illustrated in FIG. 4 in a schematic manner.

The way of drawing is illustrative also that the controlling by the control unit can be made to concern the reagent chemical inputs to the corresponding, arrow-indicated locations of the multi-ion identification device 100 in FIG. 1. Although polarity as such is not shown nor the selection, a skilled person knows from the disclosure of the embodiments that such can be made under the control of the control unit.

Although six reagent injection towers (R1, R2, R3, R4, R5, R6), also considered as reagent ion towers, are indicated in FIG. 1, where each injection tower can provide one or an ensemble of reagents in a ionized form to the ionization region, to combine with the analyte molecules from the sample, so to form adducts that are so chemically ionized, the number of the injection towers is not necessarily limited to the shown example. According to an embodiment, the polarity of each injection tower can be set individually by the control unit. According to an embodiment, a selection of user defined injection towers can be set to a certain polarity by the control unit, by using the user interface to command the actuators in the system to operate accordingly for the reagent chemical feed and/or polarity of the reagent ions.

Ionization of the reagents as such can be based on soft X-rays, corona discharge, or other suitable ionization mechanism as such to produce reagent ions for chemical ionization of the regent molecules, for combining with the analytes at the ionization region.

According to an embodiment variant, also further ionization injectors Rn, Rm can be used to provide similar ionization levels as indicated in FIG. 1 by the letters A and B at the corresponding levels in the ionization region 100b of the device 100. Such levels are denoted by the expressions An(n, n+1, n+2), Am(m, m+1, m+2). At the An and Am, the letters n and m are used as arbitrary indexes to refer to a number of injectors. Accordingly, to the classification shown in FIG. 5, the number of classes can be defined accordingly for a finer classification of the analytes and the corresponding reagents.

In schematic FIG. 4, there is an actuator illustrative box with V, X markings, which refer to the control by the control unit. The control unit in FIG. 4 can control the voltages in embodiments, used in the system by a suitable actuator being dedicated to the ionization for the reagents in each reagent injection port (R1, R2, R3, R4, R5, R6, Rn, Rm), via corona discharge, and/or X-ray tube voltage (X), but also to set the voltages for the mass spectrometer MS being controlled by the control unit, although the mass spectrometer had an independent control for its operations.

The controlling can be made according to the example in FIG. 4 by a dedicated microprocessor µP, running a controlling software, which can be embodied as a piece of software of the software packet SW. The software packet SW with the software codes for the routines are embodied as system element of the MION-system.

According to an embodiment the software packet SW comprises means to constitute a database (DB, FIG. 4) for the measurement results obtained from the mass spectrometer MS to identify the substances of a sample, and consequently the composition and abundance in the sample. Although being drawn apart from the dashed lines, the database can also be or have a part in the system's permanent part memory M.

The way of drawing the control unit and the system is selected to indicate that the control unit is controlling the system. However, the control unit is considered as a part of the system as a system element. The location can be embodied in several ways. However, according to an embodiment the control unit can be in suitable part also diversified so that some of the actuators are at the multi-ion identification device, and for example the microprocessor within the mass spectrometer, or in a network location so facilitating remote control of the system elements.

According to an embodiment the software packet SW can comprise signal processing tools to analyze the mass spectra of the mass spectrometer MS, but according to an embodiment variant also tools for cluster/group analysis, as well as for correlation calculations to find marker substances from the samples.

In other words, the software packet as a software suite consists of software services related to hardware control, mass spectrometer data analysis and user interface. The software enables use of the system with ease for the operator, as well as ensures good and consistent data quality. In addition, the software packet will perform for completing the tasks with various levels of required automation of the sampling interface, MION-inlet, mass spectrometer and data processing pipeline, to a high degree. The output of the data processing software can comprise peak lists (sets of (m/z, intensity)-pairs), to be further analyzed together with the auxiliary data, as a part of the knowledgebase. A simple dedicated user interface is embodied to guide to take a sample through the sampling process and ensure the data quality.

According to an embodiment of the present disclosure, FIG. 1 illustrates a concept of how six MION sources (reagent ion towers) can be used in parallel switching between reagent ions. The switching happens in less than 1 second and can prevent neutral reagent entry to the flow stream.

Figure 5:
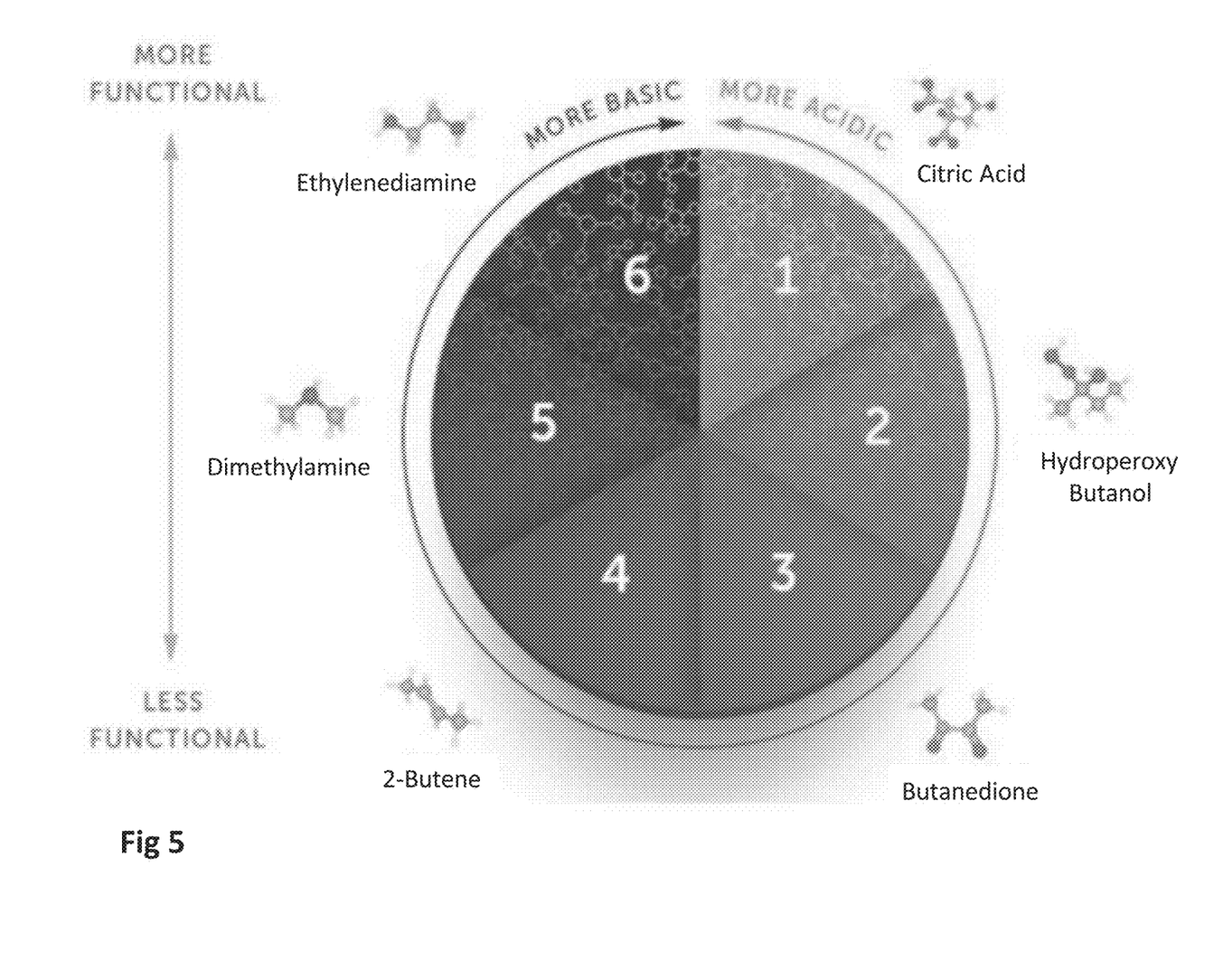
FIG. 5 is a diagram for an embodiment to group analytes for selection of reagents according to their basic-acidic properties and related functionalities to a number of groups for identification by use of an embodied multi-ion identification device.

FIG. 5 is a diagram for an embodiment to group analytes (i.e. target molecules with examples of such) for selection of reagents according to their basic-acidic properties and related functionalities to a number of groups for identification by use of an embodied multi-ion identification device.

In the example of FIG. 5, the target molecules are divided into six groups based on their chemical composition. The multi-scheme inlet developed here can cover practically all of these groups in a semi-continuous manner.

In order to target virtually every gas-phase chemical compound, there is a need for a collection of ionization reagents. With increasing functionalization of a molecule, simple molecular parameters become less well defined. A good simple example is offered by amino acids, which have characteristically both acidic and basic functionalities, with the acid-base behavior changing depending on the structure of the rest of the molecule. Thus, here we adopt an arbitrary, yet in a sense a more chemically meaningful definition, in which the molecules are labelled based on their functional group composition—and thus also on their ionization characteristics.

For such an approach variant in accordance of the present disclosure, the target molecules are divided into six groups that range from acidic, highly-oxidized and highly functionalized best detected with an adduct forming Negative Polarity Chemical Ionization (aNPCI) reagent ion (group 1), through reduced, naked hydrocarbons for which the best sensitivity is obtained by well-chosen H-transfer reagents (group 3 and 4), and finalizing again into highly functionalized, and thus also highly-oxidized, but rather basic compounds best detected with an adduct forming Positive Polarity Chemical Ionization (aPPCI) method (group 6). The biggest differences between groups 1 and 6 are the specific oxidized substituents and the nature of hydrogen bonding interactions they provide (i.e., in group 1 H-bond donors, whereas in group 6 H-bond acceptors). As illustrated, MION type of a multi-scheme inlet is able to cover all of these groups with carefully selected reagent ion combinations, which will be briefly explained next.

Group 1 reagents work almost solely with an aNPCI mode at atmospheric pressure, and the prototype reagents used here are nitrate ion (NO3-) and halogens (I—, Br—), about which the authors of the outstanding document have an extensive previous experience with. The main targets in group 1 are the most acidic and most functionalized molecules, which generally have very low gas-phase concentrations, and thus extreme selectivity and sensitivity offered by these aNPCI reagents are required. Similar characteristics are found from the group 6 target compounds (mainly the small gas-phase concentration and strong surface activity) with the important difference of being either at most only slightly acidic, or even basic. The group 6 compounds are thus best detected with an aPPCI approach (e.g., adduct formation with certain complex amine derived reagent ions). Groups 2 and 5 contain the moderately functionalized targets, which generally can sustain considerably higher gas-phase concentrations, and thus less sensitive (and selective) method is required for their quantification. An example of an aNPCI for group 2 is a carboxylic acid derived reagent ion, whereas for group 5 simple amine derived reagents are likely to work well. For the remaining least functionalized groups 3 and 4, a collection of H-transfer reagents is applied, and are formed, for example, from simple ketones and alcohols. The abovementioned reagent ions for groups 1 to 6 serve as an important example, but such grouping is not necessarily limited only to the shown instant example, which is also embodied and indicated in FIG. 4 by the optional additional injection layers illustrated by the injection layers An and Am. to be applied.

The reagent selection to correspond to the grouping can be set at the initial set up of the system and/or in an update of the system.

Figures 1B, 6, 7:
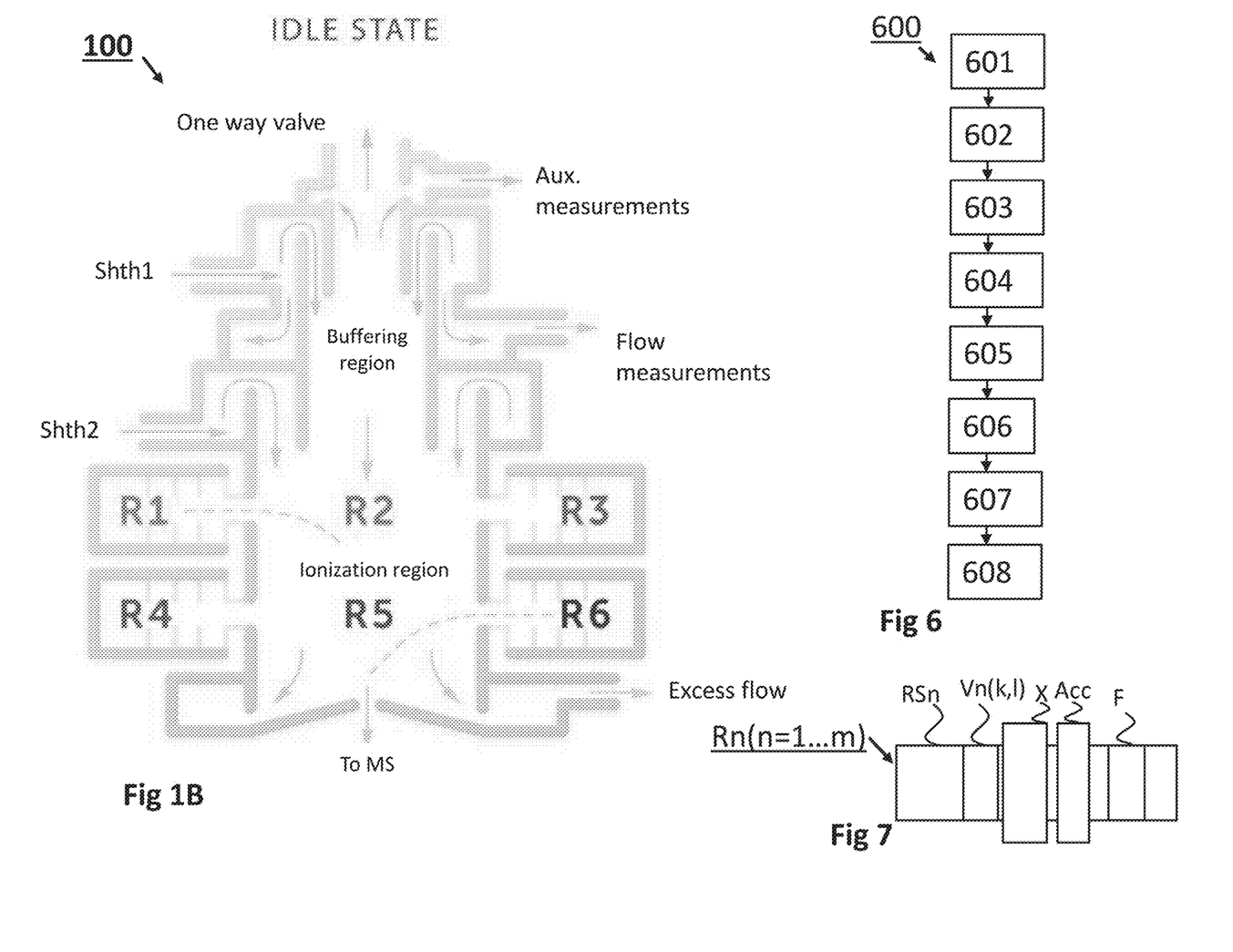
FIG. 1B illustrates the multi-ion identification device of FIG. 1 in an idle state, between consecutive sampling states of the device.
FIG. 6 is illustrating an embodiment of the invention directed to a method to identify substances from a gas sample by using MION-system.
FIG. 7 is illustrating schematically an embodied reagent ion tower structure.

According to an embodiment a method (600) using such an embodied MION-system comprises:
  sampling (601) a gas sample into a sample flow of the multi-ion identification device,
  allowing (602) turbulence to decay to laminar flow conditions of the sample flow in a buffering region of the multi-ion identification device,
  protecting (603) the gas sample by at least one or two sheath flows at least in the buffering region,
  charging (604) the gas sample constituents by reagent ion molecules formed for use in chemical ionization of said gas sample constituents to form adducts,
  allowing (605) the adduct to form from the gas sample constituents and reagent ion molecules,
  leading (606) the adducts to mass spectrometer for mass analysis,
  identifying (607) the adducts and the gas sample constituents by a software packet routine for mass analysis,
  storing (608) to a database the identification information of the gas sample constituents.

According to an embodiment, the method can comprise finding similarities from the database with similar samples, as based on identified marker substances from the previous sample mass spectra in the database. In addition, in the embodiment variant of the method, the sample associated additional data is compared to similar associated additional data of the previous samples to find correlations from the additional data and the markers between the instant and previous gas samples.

According to an embodiment, the comparison is made by the software packet as a system element. According to an embodiment variant the comparison comprises at least one of the following being used in it: an artificial intelligence algorithm to find patterns between the addition data and the marker substances, self-learning algorithm to assist the artificial intelligence algorithm, and neural network for optimization of the finding the marker substances.

FIG. 7 illustrates an embodied reagent ion tower structure. The reagent ion tower in question can be R1, R2, R3, R4, R5, R6, Rn, Rm, which is illustrated by the expression Rn(n=1 . . . m). RSn denotes to a dedicated source of reagent, $v_n(k,l)$ denotes to a dedicated valve to control the reagent RSn feed, X denotes to charger, independently is the charger embodied by soft X-rays, corona discharge, electrospray or a combination thereof. The polarity can be changed between negative positive and neutral according to the control unit settings. Acc denotes to an accelerator of charged reagent ions, which can be implemented by electric fields. In addition, the reagent ion tower can comprise also a filter F, to filtrate unwanted polarity and/or charge carrying ions away from the reagent ion tower output. According to an optional embodiment, the electric filter can be embodied within the accelerator Acc as integrated.

Consequently, a skilled person may, on the basis of this disclosure and general knowledge, apply the provided teachings in order to implement the scope of the present invention as defined by the appended claims in each particular use case with necessary modifications, deletions, and additions.

The invention claimed is:

1. A multi-ion identification device comprising:
  a first plurality of reagent ion towers (R1, R2, R3) to provide ionization reagent ions each, in a first plane (IR(A)) perpendicular to sample flow entrance direction to ionization region of the multi-ion identification device (100) in angularly equal distribution in respect to a central axis line (C), emitting lines (L1), (L2), (L3) of the first plurality of reagent ion towers having an off-set (a) to deflect from the direction of the central axis line (C) along the respective emitting lines (L1), (L2), (L3) of the first plurality of reagent ion towers; and a second plurality of reagent ion towers (R4, R5, R6) to provide ionization reagent ions each, in a second plane (IR(B)) perpendicular to sample flow entrance direction to ionization region of the multi-ion identification device (100) in angularly equal distribution in respect to the central axis line (C), emitting lines (L4), (L5), (L6) of the second plurality of reagent ion towers having an off-set (a) to deflect from the direction of the central axis line (C) along the respective emitting lines (L4), (L5), (L6) of the second plurality of reagent ion towers, wherein said first plane (IR(A)) and second plane (IR(B)) are parallel to provide a reaction time for the ions emitted from the respective reagent ion towers to chemically ionize analyte molecules in the sample, the so formed adducts being transported from the ionization region to a mass spectrometer port for mass analysis of the species of the adducts.

2. The multi-ion identification device of claim 1, wherein each ionization reagent of the respective reagent ion tower in same plane (IR(A)) is configured to operate according to same ion production mechanism to provide respective reagent ions from a dedicated reagent ion tower.

3. The multi-ion identification device of claim 1, wherein the ionization mechanism of a reagent ion tower is at least one of the following: X-ray, soft-X-ray, corona discharge, electrospray, xenon uv lamp, based ionization mechanism.

4. The multi-ion identification device according to claim 1, wherein the polarity of a reagent ion tower produced ions are adjustable to positive or negative ions.

5. The multi-ion identification device according to claim 1, wherein at least one of the reagent ion towers comprises a filter to filter away multiple charged reagent agents away from entry to the ionization region.

6. The multi-ion identification device according to claim 1, wherein the ionization region comprises a round cylindrical symmetry with a central axis line (C) as a symmetry center.

7. A multi-ion identification device comprising:
a first plurality of reagent ion towers (R1, R2, R3) to provide ionization reagent ions each, in a first plane (IR(A)) perpendicular to sample flow entrance direction to ionization region of the multi-ion identification device (100); and
a second plurality of reagent ion towers (R4, R5, R6) to provide ionization reagent ions each, in a second plane (IR(B)) perpendicular to sample flow entrance direction to ionization region of the multi-ion identification device (100),
wherein said first plane (IR(A)) and second plane (IR(B)) are parallel to provide a reaction time for the ions emitted from the respective reagent ion towers to chemically ionize analyte molecules in the sample, the so formed adducts being transported from the ionization region to a mass spectrometer port for mass analysis of the species of the adducts, and
wherein the reagent ion towers (R1, R2, R3) are aligned in a plane (IR(A)), and have an off-set (a) to deflect from the direction of a central axis line (C) along the respective emitting lines (L1, L2, L3).

8. A multi-ion (MION) identification system (Sys) comprising:
at least one multi-ion identification device according to claim 1,
control unit to control the multi-ion identification system and the multi-ion identification system's actuators for the operation in mass analysis of adducts formed from the constituents of the sample,
a mass spectrometer (MS) to make said mass analysis,
a database (DB) to store and process mass analysis results.

9. The multi-ion identification system of claim 8, wherein the system comprises a software packet (SW) configured to control operation of the multi-ion identification system.

10. The multi-ion identification system of claim 8, wherein the system comprises such a software packet (SW) that is configured to make group analysis to find and deduce marker substances from the results.

11. The multi-ion identification system of claim 10, wherein the software packet (SW) comprises at least one of the following: a machine learning algorithm, a neuron network solver for classification and optimization of data clusters, an artificial intelligence algorithm, an elastic net regressions algorithm, random forests and recursive feature elimination algorithm, to be used to analyze, compare and predict chemical features of gaseous samples.

12. The multi-ion identification system of claim 8, wherein the system comprises an ion detector to detect ions, said ion detector being configured to simultaneously utilize multiple selective ion chemistries both in negative and positive modes of detection.

13. The multi-ion identification system of claim 8, wherein the system is configured to detect extremely low vapor pressure, highly oxidized multifunctional organic molecules (HOM) from the sample.

14. A method identifying substances from a gas sample by using the multi-ion system (MION-system) of claim 8, comprising:
sampling a gas sample into a sample flow of the multi-ion identification device,
allowing turbulence to decay to laminar flow conditions of the sample flow in a buffering region of the multi-ion identification device,
protecting the gas sample by at least one or two sheath flows at least in the buffering region,
charging the gas sample constituents by reagent ion molecules formed for use in chemical ionization of said gas sample constituents to form adducts,
allowing the adduct to form from the gas sample constituents and reagent ion molecules,
leading the adducts to mass spectrometer for mass analysis,
identifying the adducts and the gas sample constituents,
storing to a database the identified gas sample constituents.

15. The multi-ion identification device of claim 2, wherein the ionization mechanism of a reagent ion tower is at least one of the following: X-ray, soft-X-ray, corona discharge, electrospray, xenon uv lamp, based ionization mechanism.

16. The multi-ion identification device according to claim 2, wherein the polarity of a reagent ion tower produced ions are adjustable to positive or negative ions.

17. The multi-ion identification device according to claim 3, wherein the polarity of a reagent ion tower produced ions are adjustable to positive or negative ions.

18. The multi-ion identification device according to claim 2, wherein at least one of the reagent ion towers comprises a filter to filter away multiple charged reagent agents away from entry to the ionization region.

19. The multi-ion identification device according to claim 3, wherein at least one of the reagent ion towers comprises a filter to filter away multiple charged reagent agents away from entry to the ionization region.

20. A multi-ion identification device comprising:
- a first plurality of reagent ion towers (R1, R2, R3) to provide ionization reagent ions each, in a first plane (IR(A)) perpendicular to sample flow entrance direction to ionization region of the multi-ion identification device (100); and
- a second plurality of reagent ion towers (R4, R5, R6) to provide ionization reagent ions each, in a second plane (IR(B)) perpendicular to sample flow entrance direction to ionization region of the multi-ion identification device (100),
- wherein said first plane (IR(A)) and second plane (IR(B)) are parallel to provide a reaction time for the ions emitted from the respective reagent ion towers to chemically ionize analyte molecules in the sample, the so formed adducts being transported from the ionization region to a mass spectrometer port for mass analysis of the species of the adducts, and
- wherein at least one of the reagent ion towers comprises a filter to filter away multiple charged reagent agents away from entry to the ionization region.

* * * * *